United States Patent [19]
Littlejohn et al.

[11] Patent Number: 5,798,981
[45] Date of Patent: Aug. 25, 1998

[54] INTEGRITY ASSESSMENT OF GROUND ANCHORAGES

[75] Inventors: Gavin Stuart Littlejohn, York, England; Albert Alexander Rodger, Aberdeen, Scotland

[73] Assignees: Aberdeen University, Scotland; The University of Bradford, England

[21] Appl. No.: 725,887

[22] Filed: Oct. 4, 1996

[30] Foreign Application Priority Data

Apr. 6, 1994 [GB] United Kingdom ............... 9406745

[51] Int. Cl.$^6$ .................... G01N 29/04; E02D 33/00
[52] U.S. Cl. .................... 367/13; 73/594; 73/579
[58] Field of Search ............... 367/13; 73/579, 73/581, 594

[56] References Cited

U.S. PATENT DOCUMENTS

| | | | |
|---|---|---|---|
| 4,062,229 | 12/1977 | Godfrey et al. | 73/582 |
| 4,152,929 | 5/1979 | Edmond et al. | 73/581 |
| 4,198,865 | 4/1980 | Tarpley, Jr. et al. | 73/582 |
| 4,359,890 | 11/1982 | Coelus | 73/12.13 |
| 5,165,270 | 11/1992 | Sansalone et al. | 73/12 |

FOREIGN PATENT DOCUMENTS

WO 95/27831  10/1995  WIPO.

OTHER PUBLICATIONS

Hatzipantelis et al. "the Use of Hidden Markof Models for Condition Monitoring Electrical Machines", Proc. EMD, Institute of Electrical Engineering Conference on Electrical Machine Drives, Sep. 1993.

Penman et al. "The Application of Artificial Neural Networks in Identifying Faults in Induction Machines", Proceeding of ICEM No. 8, Sep. 1992, pp. 1256–1260.

Bolstad et al. "US Bureau of Mines Rock Bolting Research", Proc. Int. Symp. on Rock Bolting, Abisko, AA Balkema, Rolterdam, Sep. 1983, pp. 313–320.

Tadolini, "Mine Roof Bolt Load Determinations Utilizing Ultrasonic Management Systems", CIM Bulletin vol. 3, pp. 49–54, 1990.

British Standard Code of Practice for Ground Anchorages BS 8081: 1989.

*Primary Examiner*—Ian J. Lobo
*Attorney, Agent, or Firm*—Laubscher & Laubscher

[57] ABSTRACT

A method and apparatus for monitoring the condition of a ground anchorage including a tendon arranged in a bore in a group formation at a site is characterized by detecting the vibrational response signature of the anchorage to an impulse load. The vibrational response signature to the impulse is recorded and compared with a reference signature from which any changes in the integrity of the anchorage can be determined.

14 Claims, 6 Drawing Sheets

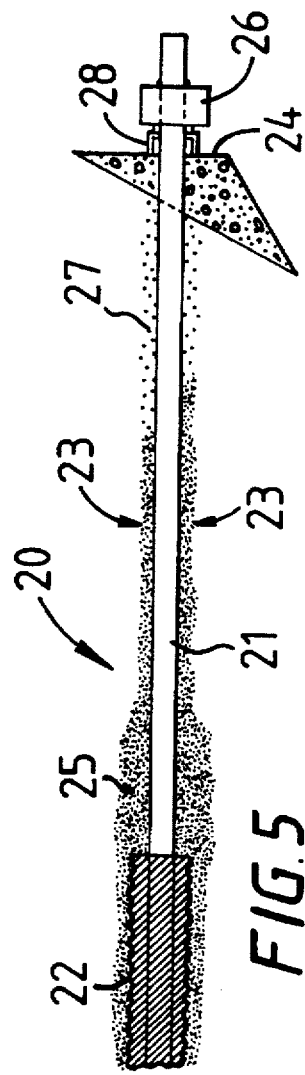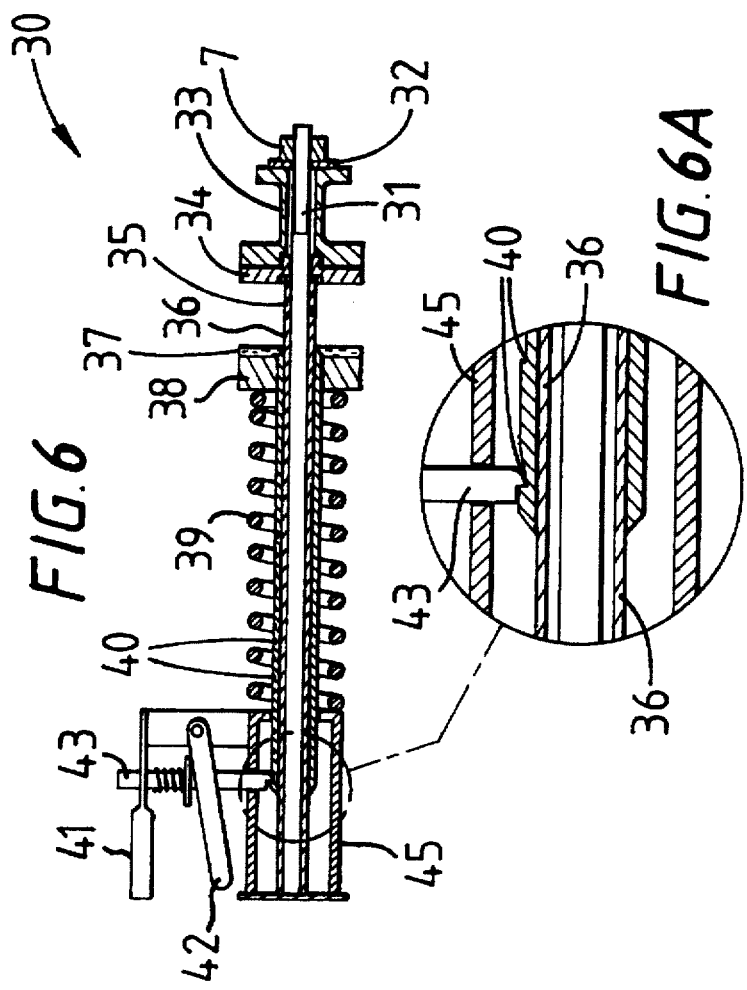

5,798,981

INTEGRITY ASSESSMENT OF GROUND ANCHORAGES

This application is a continuation of PCT/GB 95/00789 filed Apr. 5, 1995 and which designates the United States of America.

BACKGROUND OF THE INVENTION

The present invention relates to the non-destructive integrity assessment of ground anchorages as defined and described in the British standard BS8008:1989.

The assessment of the condition and integrity of ground anchorages used to solve problems involving direct tension, sliding, overturning, dynamic loading and ground pre-stressing relating to engineering works is an ongoing problem. For works such as cliff stabilization, tunnels, underground caves and dams it is common to secure a ground anchorage in a solid formation such as rock to provide resistance to withdrawal or restrict ground movement with time.

In the case of rock support, anchorages are usually formed by drilling the formation to a depth of, for example, 6 meters, and inserting in the so-formed bore a grout which may be either resin or cement-based with a metal tendon in the form of a rod, strand or wire used either singly or in a group with an anchor head, post tensioned and secured under tension. These systems work satisfactorily to retain the rock formation in a desired configuration over time.

There are several types of ground anchorages of which the most common are defined and described in BS8081:1989. These are shown in FIGS. 7A to 7D in the accompanying drawings. Briefly the ground anchorages of 7A and 7B are more commonly used in rock while those of 7C and 7D are more usually used in softer ground.

FIG. 7A shows a typical rock bolt fully bonded over its free anchor length. Specifically an elongate anchor (a) is disposed in a bore (b) fixed by a primary grout (c) with its remaining length disposed in a secondary grout (d). Accordingly the length of the primary grout provides a fixed anchor length (e) while the length of the secondary grout provides a free anchor length (f). The anchor is retained by an anchor head (g).

FIG. 7B shows a similar arrangement but which differs in that the free anchor length (f) is a region in which the elongate anchor (a) is not in contact with the grout to form a decoupled tendon region (i). The anchor (a) is fixed in the bore (b) by a grout encapsulation (h) As will be seen the anchor (a) is specially formed over the portion thereof forming the fixed anchor length (e) to provide good adherence.

FIG. 7C shows a ground anchorage most suited to softer ground. Similarly to the above, the anchor (a) is disposed in a bore or shaft (b). The remote end of the anchor (a) is formed with an encapsulation (h) of a length (k) about which is disposed a grout (d) which encapsulates the remote end of the anchor (a) and extends to a void or collapsed zone (l). This gives a ground anchorage in soft ground stressed by an anchor head (g). This anchorage therefore may be defined by a free anchor length (f), a shaft length (m), a fixed anchor length (e), and an anchor bond length (n).

Finally, FIG. 7D shows a similar ground anchor (a) of a simpler (temporary) construction which provides an enlarged ground region (d) but wherein the encapsulation (h) is not required. The anchor head (g) is shown with a stressing jack (o) in situ.

However, with time, due to the consolidation of the rock mass or movements along discontinuities arising in rock formations, loss of tension may occur and/or the grout may begin to fail and lose bond, and/or the tendon may be subject to corrosion. These features can give rise to a situation where the ground anchorage begins to yield or fail, which could potentially lead to catastrophic failure of the surrounding engineering works. At the very least it could give rise to unacceptable ground movements which could lead to structural damage.

Another type of ground anchorage which is suitable for a softer formation such as soil may be used, for example, for retaining walls. In this arrangement a relatively large bore is inserted into the formation and a resin or cement encapsulation is bonded to the remote and of the tendon. A portion of the borehole may then be filled With, for example, cement-based grout. The intervening ground formation then tends to collapse into any remaining void so formed, particularly with time, thereby retaining the anchorage in situ. The invention applies equally to these anchorages.

BRIEF DESCRIPTION OF THE PRIOR ART

Previously, the testing of ground anchorages has been a laborious process. It has required load monitoring via load calls, or load testing using hydraulic jacks; both are expensive and the latter is time consuming. For this reason only about 5% of established anchorages are monitored, and indeed the results obtained provide only limited information on the actual integrity of an anchorage.

NDT systems for the integrity testing of rock bolts have previously been proposed by Bolstad DD et al in U.S. Bureau of Mines, Rock Bolting Research, Proc Int Symp on Rock Bolting, Abisko, AA Balkema. Rotterdam pp 313 to 320 September 1983, and by Tadolini SC. Mine Roof Bolt loading determinations using Ultrasonic Measurement Systems, CIM Bulletin, Vol 3 pp 49–54 1990.

However, such prior art methods only provide a qualitative description of the anchorage condition in terms of bonding, or require drilling of target holes in the bar tendon before installation. Consequently such systems have not been used widely in practice.

From GB-A-1 593 811 a method of testing the integrity of the anchoring of a rock bolt is known involving measuring the vibration response to broadband axial and/or transverse vibrations resulting from a compressive impulse load. Examination of resonant frequencies is employed to infer rock bolt condition. This known method requires a conversion of resonant frequency to grouted bolt length using known data for the bolt size and diameter. An inherent problem that occurs with this approach is that co-vibrating mass of rook will influence the results. Due to the variability of rock conditions within, for example, tunnels, particularly if the tunnel being supported is being formed by blasting, the co-vibrating rock mass can vary significantly in dynamic properties between bolts. This variability makes this approach to integrity assessment very difficult to apply. Moreover, it is noticeable that this method does not only take into account rock properties.

The present invention results from the observation that the signature of the frequency response spectra of ground anchorage responding to different blasts, and at different distances from the blast, were found to be of similar form.

SUMMARY IF THE INVENTION

The inventors therefore concluded that the response spectra depended in large measure on the form of ground anchorage construction, and the characteristics of the co-vibrating rock mass. Thus it was considered that by an analysis of the signature of the response spectra, and/or through the use of time domain signals, the integrity of the ground anchorage in a solid formation could be assessed. This assessment may be quantified by comparison with a database of response spectra signatures to provide an indication of changes in anchorage integrity.

According therefore to a first aspect of the present invention there is provided a method for monitoring the condition of a ground anchorage in a bore in a solid formation at a site, which method comprises:

securing a device for monitoring frequency response spectra to the ground anchorage, applying to the ground anchorage an impulse load of a predetermined value, recording the signature of the frequency response spectra, and comparing the signature with a reference signature from the site, thereby to obtain an indication of the integrity of the ground anchorage in the formation.

The reference frequency signature may be pre-recorded values obtained from intact ground anchorages, anchorages with known defects, and values for the ground anchorage obtained immediately after installation, and subsequently following the application of impulse forces. Preferably, the impulse load applied to the anchorage is tensile.

The signature of the frequency response spectra for any given anchorage type is affected by tendon length, decoupled length, tensile load and the nature of the rock mass, and thus the most valuable information comes from an analysis of changes in the signature of the spectral frequency with time at the same anchorage, but also valuable information can be gleaned from initial frequency signature spectral analysis data since this can show for example if rock has fractured significantly after stressing, or if for some reason rapid debonding has occurred.

The solid formation may be mudstone or granite, for example. It will be appreciated that the signature of the frequency response spectra from these formations will be different, but will remain substantially the same over time so that the signature of the spectra from intact mudstone after a period of, for example, five years, will remain substantially constant unless changes such as fracturing have taken place.

It follows that changes in the aspects of the spectral data with time can be used to indicate early signs of structural failure.

In a second aspect of the present invention there is provided an apparatus for carrying out the method defined above for monitoring the condition of a ground anchorage in a bore in a solid formation, the apparatus comprising:

an impulse plate provided with a device for operative interconnection to an anchor head, a device for imparting a predetermined impulse load to the impulse plate, a detecting device operatively associated with the impulse plate, a signal conditioner adapted to record and/or process an output signal from the detecting device.

Preferably the display device includes a computer programmed to display a visual representation of the spectral data, the computer and/or conditioner also being adapted to include a comparison device for comparing the spectral data obtained, with previously recorded spectral data. The apparatus may also be provided with an indicator for indicating a relative condition of the ground anchorage resultant from said comparing step.

The detecting device may be an accelerometer, a geophone or a linear variation differential transfer (LVDT) device.

The device for imparting an impulse load may be a spring loaded hammer adapted to impart a standardized load. The device for imparting an impulse load may be substantially coaxial with the ground anchorage. The impulse load imparted is preferably just enough to actuate the entire length of the ground anchorage and allow accurate recording.

The computer may be provided with a neural network. The uses of neural networks have been explored inter alia in "The Application of Neural Networks in Identifying Faults in Induction Machines", Penman J and Yin CM; Proceedings of ICEM No. 8, Sep. 1992 pp 1256 to 1260; and in "The Application of Hidden Markov Models for Condition Monitoring"; Penman J and Hatzipantellis E, Proc. EMMD Institute of Electrical Engineering. Conference on Electrical Machine Drives; September 1993, both of which are incorporated herein by reference.

Techniques involving the use of neural networks are well suited to applications such as this where existing data provide sets of learning pairs. In such circumstances the complexities and non-linearities inherent in the responses to the test stimuli can be identified using either supervised or non-supervised networks, and once trained, diagnosis can be virtually instantaneous.

Initially spectral responses to stimuli are used as a basis for learning, but also time domain data may be utilized directly. This allows the removal of an additional layer of signal processing with a commensurate reduction in system costs.

Both perception and feature map architectures are suitable for use in the neural networks described above. The perception based networks are more effective at separating more well-developed cases of degraded performance, but feature map architectures can give an early indication of atypical behaviour. The perception and feature map architectures may be used together or sequentially, but both provide the possibility of a wider examination of all derived data simultaneously.

The Use of artificial neural networks in the present invention is particularly effective in signal processing and situations such as this where the signals are rich in structural detail.

BRIEF DESCRIPTION OF THE FIGURES

The invention will now be described, with reference to the accompanying drawings, by way of example only.

FIG. 5 shows a second type of ground anchorage for test by the methods of the invention in diagrammatic transverse cross-section;

FIG. 6 shows in transverse cross-section an impulse load imparting device;

FIG. 6A shows an enlarged cross-section of a trigger for the device of FIG. 6, and FIGS. 7A, 7B, 7C and 7D show ground anchorages of different types as approved in BS8081:1989.

DETAILED DESCRIPTION

Figure 1:
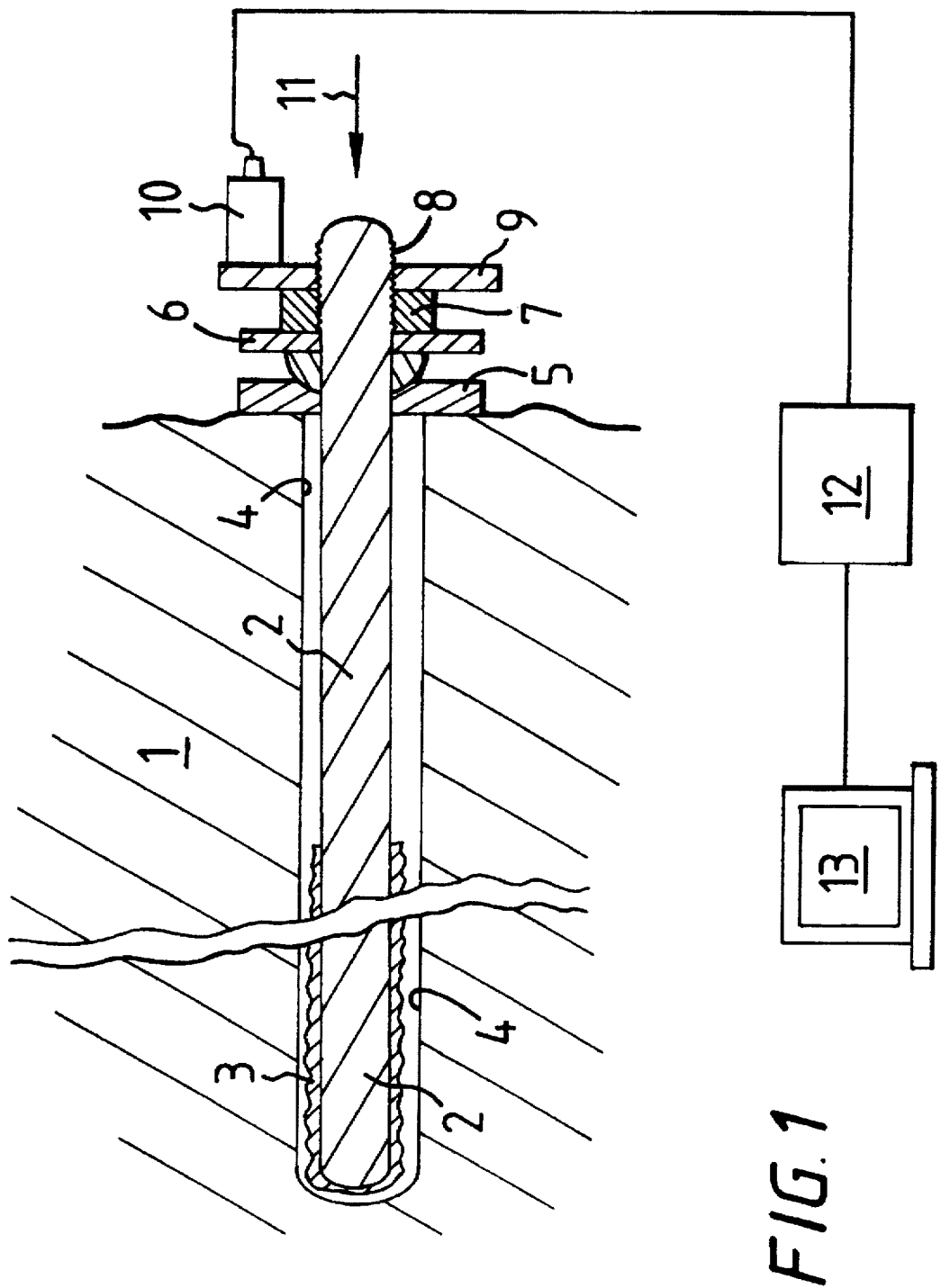
FIG. 1 shows a transverse cross-section through an in situ ground anchorage in a rook formation with the testing apparatus of the invention applied.

With reference to FIG. 1 a ground face or structure 1 is penetrated by, for example, a bore (4). The bore (4) has a diameter greater than the diameter of a steel tendon and accordingly the steel tendon (2) may be inserted into the bore (4) with or without a resin-based, or cement-based, grout encapsulation (3), the encapsulation then being bonded to the surrounding ground by further grout. Once the grout has set, a collar assembly (anchor head) (5) may be positioned against the ground face and about the steel tendon (2), whereupon a washer (6) may be positioned thereagainst. The tendon (2) may then be tensioned and retained in position by means of a nut (7) co-operating with a screw thread (8).

In accordance with the present invention an impulse plate (9) is located upon the head of the tendon (2) and retained thereupon by engagement with the screw thread (8), but it may be located by bolting, clamping or other convenient means. The impulse plate (9) bears thereupon an accelerometer (10).

An impulse load imparting device shown generally at (11) is than operatively associated with the impulse plate (9) (as shown in FIGS. 6 and 6A).

The accelerometer (10) is connected to a signal conditioning and recording device (12) which, in turn, is connected to a computer with monitor screen (13).

In use, the impulse load of a predetermined value (11) is caused to impact upon the head of the steel tendon (2) thereby generating frequency response spectra which are converted into a signal by means of the accelerometer (10) and passed to the signal conditioning and recording unit (12).

The recording unit (12) both records the data for future use and may also input the data in raw or conditioned form to the computer (13). This may have been provided with an earlier reading from the steel tendon (2) and accordingly the new data can be compared with the old data utilizing a neural network program. If any substantive changes are recorded and the program recognizes these as indicative of, for example, debonding, changes in prestress, or localized corrosion of the steel tendon, a warning can be suitably generated. The warning may be visible, audible or both.

Figure 2:
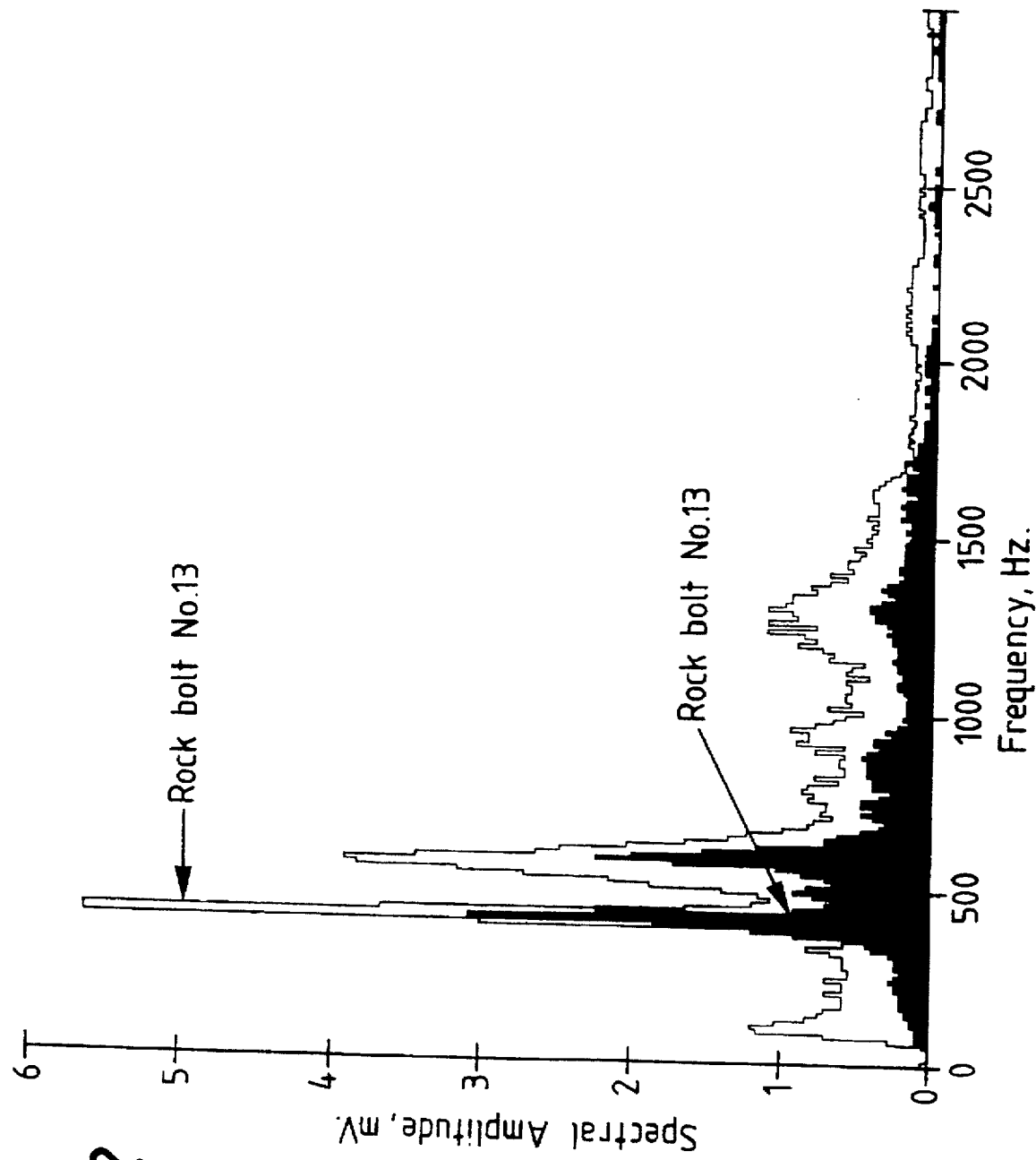
FIG. 2 shows a graph of an anchor head acceleration spectra showing frequency against spectral amplitude in mV.

Evidence justifying the validity of this approach may be seen from the spectral data exhibited in FIG. 2. These two spectra were obtained from tests at the Pen Y-Clip Tunnel which were effected in 1991 in North Wales. This relates to a major rock tunnel constructed using blasting techniques. Primary support for much of the tunnel was provided by resin bonded rock bolt anchorages. At this site axial load and acceleration were measured on anchorages positioned at various distances from a blast face. The influence of bolt length and tensile load on rock bolt performance was investigated, as were the differences in bolt response resulting from the use of single speed rather than two speed resin bonding processes.

In FIG. 2 tests show the response of the same anchorage (rock bolt 13) to blasts at different distances from it. The main frequency components are the same in both spectra indicating that the spectral signature is a characteristic of the constructed anchorage. Spectra obtained from the response of a number of anchorages to the same blast may be compared by using a three-dimensional representation which takes account of chainage from the blast face and load in the anchorage. In deriving such a representation it is valuable to employ "relative" or "normalized" spectra and to display these in terms of spectral energy density (ESD) as shown in FIGS. 3 and 4.

Figure 3:
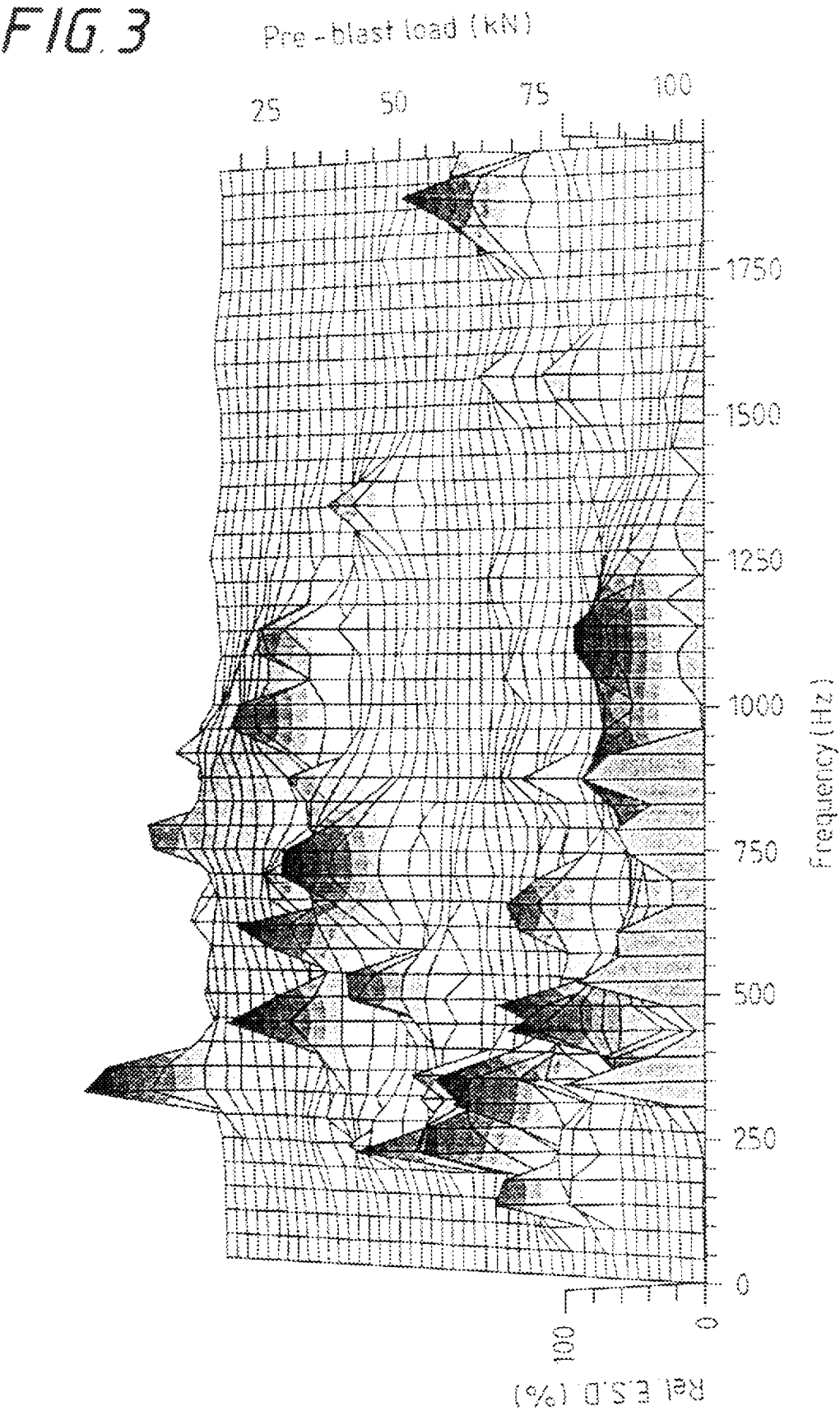
FIG. 3 shows a graph of the relationship between the spectral energy density (ESD), frequency and pre-blast load (in kN) on a normal anchorage showing higher frequency peaks to the right hand side of the graph.

FIG. 3 indicates, for example, that higher frequency components are less dominant at higher tensile loads. Analysis of the results gained have shown therefore that the signature of the spectra is affected by bolt length, decoupled length, tensile load, and the nature of rock mass, but given that these are the same, as they will be for any given anchorage, signal changes are indicative of significant changes which can be quantified by the method and apparatus of the invention.

Figure 4:
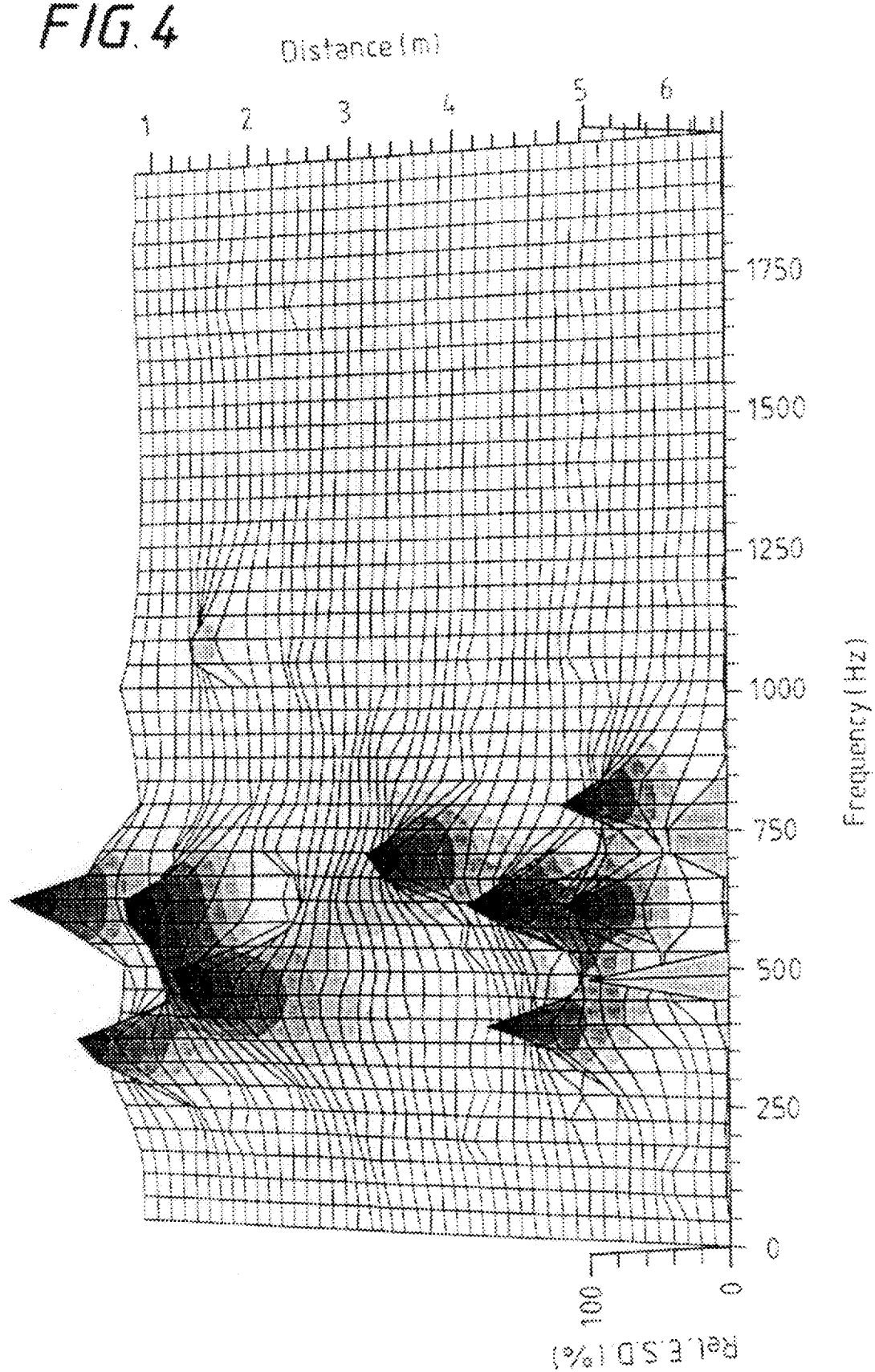
FIG. 4 shows a graph of the relationship between the ESD, frequency and pre-blast load (in kN) on a partially debonded anchorage showing loss of higher frequency peaks.
Figure 7A:
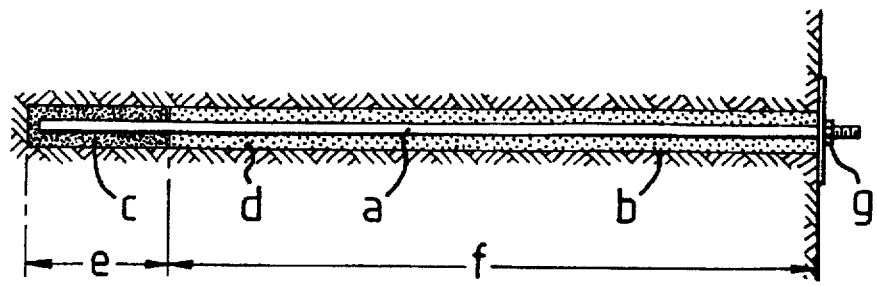
Figure 7B:
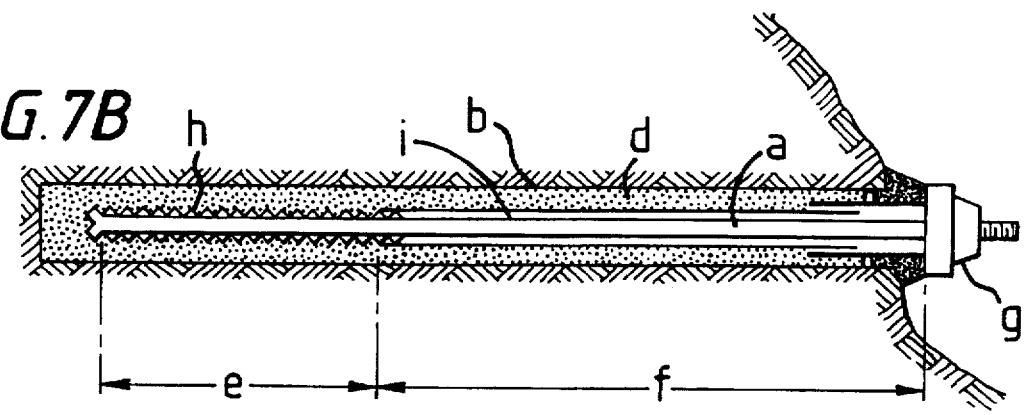
Figure 7C:
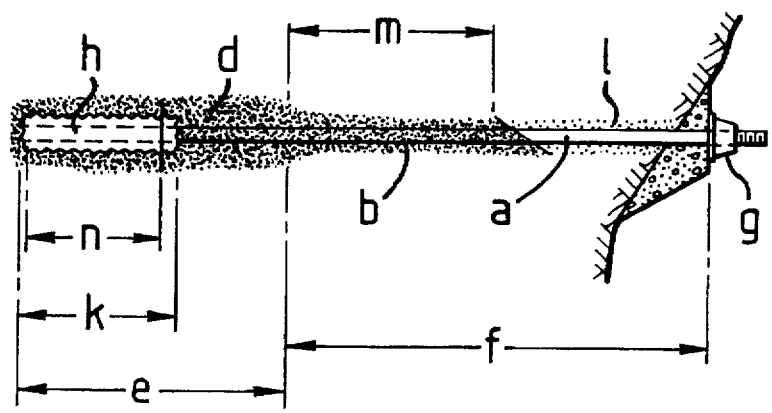
Figure 7D:
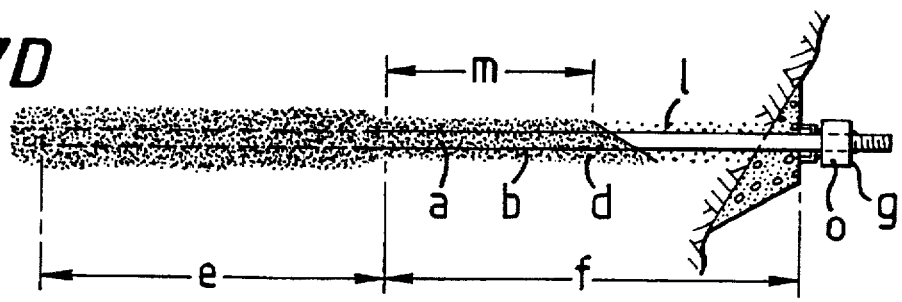

FIG. 4 representing tests on a partially bonded anchorage shows fewer peaks to the right hand side of the graph indicating that loss of bond is reflected by a change in the spectral characteristics. An analysis by a neural network will compare the graphs of FIGS. 3 and 4 and quickly indicate a loss of pre-stress.

FIG. 5 shows a ground anchorage (20) for a retaining wall. The ground anchorage (20) comprises a tendon (21) extending the length of the anchorage which is placed inside the large bore (22) in the ground formation. The tendon may or may not terminate at its remote end in a resin nor cement-based grout encapsulation. The tendon is then grouted (bonded) to the surrounding ground to provide a fixed anchor. When this grout (25) has set to the necessary degree an anchor head (24) is formed adjacent the near end of the tendon (2) by which load will eventually be imparted to the ground formation (27). It will be appreciated that a portion of the bore formed in the formation will not be filled with grout and this tends to collapse over a zone (23).

When the ground anchorage (20) has fully hardened a stressing jack (26) is clamped upon the protruding end of the tendon (21) at the anchor head and subjected to an axial force to post-tension the tendon (21). Thereupon a fixing nut or wedge assembly (28) is incorporated and allowed to become embedded in the ground anchorage (20) thereby retaining the tensile load.

It will be appreciated that this type of ground anchorage is utilized more commonly in softer ground formations but may equally be tested in the same way as the rock bolt formations previously described. The monitoring is effected in exactly the sate way.

As shown in FIG. 1 the impulse load shown generally at (11) is applied to an impulse plate (9) bearing an accelerometer (10) thereupon.

As shown in FIG. 6 an impulse load device (30) may be employed to provide the impulse load (11) of FIG. 1. This impulse load imparting device (30) is formed upon the end of a tendon (31). Tendon (31) is provided, as shown in FIG. 1, with a nut (7) but the impulse plate (9) shown in FIG. 1 is replaced by an annular load cell (33) which fits about the end of the steel tendon (31). The and of the annular load cell (33) remote from the ground anchorage head is provided with an outwardly directed flange which is formed coaxially with an impact plate (34) about a rubber coupling (35). The rubber coupling (35) terminates in a stress-tube or chair (36) which extends co-axially from the annular load cell (33).

The stress-tube (36) has formed thereabout a radially extending hammer member (38) provided with a cork pad (37). A spring (39) loads the hammer (38) against a collar (45). The collar (45) comprises a trigger device (41) provided with an actuator (42) and reciprocating spring loaded release bar (43). The exterior of the stress-tube (36) is also provided with a pair of axially spaced detents (40), for a purpose to be elucidated later.

As shown in FIG. 6 the hammer (38) is shown primed to a first position to impart a small impulse load. With the impulse loading device secured upon the protruding end of the tendon (31), the actuator (42) is urged towards the trigger device handle (41) thereby urging the reciprocating bar (43) to move away from the detent (40) thereby releasing the hammer (38). The hammer (38) is then driven by means of spring (39) such that the cork pad (37) contacts the impact plate (34) thereby imparting a load to the protruding head of the steel tendon (31). A larger load can be imparted by causing the reciprocating bar (43) to contact the lower of the detents (40).

The act of initiating the impulse load may also initiate recording by a neural network. The act of imparting the load and the signals generated thereby can all be recorded and displayed graphically. By this means small irregularities in the level of the impulse load can be compensated by means of correctly written software.

The invention therefore provides an apparatus for monitoring the condition over time of a ground anchorage in a formation and to a method for utilizing such an apparatus.

We claim:

1. A method for monitoring the condition of a ground anchorage comprising a tendon arranged in a bore in a ground formation at a site, comprising the steps of
   (a) securing an impulse plate to the head of the tendon;
   (b) applying an impulse load of a predetermined value to said impulse plate;
   (c) detecting the vibrational response signature of the ground anchorage to the impulse load;
   (d) recording the detected vibrational response signature; and
   (e) comparing the detected vibrational response signature with a ground anchorage reference vibrational response signature for the site, thereby to obtain an indication of the integrity of the ground anchorage.

2. A method according to claim 1, wherein the ground anchorage reference vibrational response signature is obtained immediately after installation of a ground anchorage at the site and prior to tensioning and/or immediately after tensioning thereof.

3. A method according to claim 1, wherein the detected vibrational response signature is compared with an earlier recorded vibrational response signature from the ground anchorage to provide an indication of changes in the integrity of the ground anchorage over time.

4. A method according to claim 1, wherein the impulse load applied to the ground anchorage is tensile.

5. A method according to claim 1, wherein the vibrational response signature is detected by an accelerometer, a geophone or a linear variation differential transfer device.

6. A method according to claim 1, wherein the step of comparing the detected vibrational response signature with the ground anchorage reference vibrational response signature is effected by a neural network.

7. An apparatus for monitoring the condition of a ground anchorage comprising a tendon arranged in a bore in a ground formation at a site, comprising:
   (a) an impulse plate connected with a head of the tendon;
   (b) means for imparting a predetermined impulse load to said impulse plate;
   (c) detecting means for detecting the vibrational response signature of the ground anchorage to said impulse load;
   (d) recording means connected with said detecting means for recording the detected vibrational response signature; and
   (e) means connected with said recording means for comparing the detected vibrational response signature with a ground anchorage reference vibrational response signature for the site.

8. An apparatus according to claim 7, wherein the ground anchorage reference vibrational response signature is obtained immediately after installation of a ground anchorage at the site and prior to tensioning and/or immediately after tensioning thereof.

9. An apparatus according to claim 7, wherein said means for comparing the detected vibrational response signature comprises a computer.

10. An apparatus according to claim 9, wherein said computer is programmed to display a visual representation of the detected vibrational response signature.

11. An apparatus according to claim 9, wherein said computer is programmed to compare the detected vibrational response signature with an earlier recorded vibrational response signature from the ground anchorage to provide an indication of changes in the integrity of the ground anchorage over time.

12. An apparatus according to claim 9, wherein said computer is provided with a neural network program.

13. An apparatus according to claim 7, wherein said detecting means is selected from an accelerometer, a geophone or a linear variation differential transfer device.

14. An apparatus according to claim 7, wherein said means for imparting an impulse load comprises a spring loaded hammer adapted to impart a standardized load.

* * * * *